(12) United States Patent
Hüfner et al.

(10) Patent No.: US 11,390,855 B2
(45) Date of Patent: Jul. 19, 2022

(54) SYNTHESIS OF FUCOSYLATED COMPOUNDS

(71) Applicant: Chr. Hansen HMO GmbH, Rheinbreitbach (DE)

(72) Inventors: Eric Hüfner, Hennef (DE); Julia Parkot, Cologne (DE); Stefan Jennewein, Aachen (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 0 days.

(21) Appl. No.: 16/440,777

(22) Filed: Jun. 13, 2019

(65) Prior Publication Data

US 2019/0382737 A1 Dec. 19, 2019

Related U.S. Application Data

(62) Division of application No. 13/140,548, filed as application No. PCT/EP2009/067531 on Dec. 18, 2009, now abandoned.

(30) Foreign Application Priority Data

Dec. 19, 2008 (EP) ..................................... 08172267

(51) Int. Cl.
*C12N 9/12* (2006.01)
*C12N 9/10* (2006.01)
*A23L 33/00* (2016.01)

(52) U.S. Cl.
CPC ............... *C12N 9/12* (2013.01); *A23L 33/00* (2016.08); *C12N 9/1051* (2013.01); *A23V 2002/00* (2013.01)

(58) Field of Classification Search
CPC ................................ C12N 9/1051; C12N 9/12
See application file for complete search history.

(56) References Cited

U.S. PATENT DOCUMENTS

| | | | |
|---|---|---|---|
| 7,326,770 B2 | 2/2008 | Simala-Grant et al. | |
| 7,893,041 B2 | 2/2011 | Morrow et al. | |
| 2008/0145899 A1 | 6/2008 | Johnson et al. | |

FOREIGN PATENT DOCUMENTS

| | | |
|---|---|---|
| EP | 1 275 714 A1 | 1/2003 |
| EP | 1 426 441 A | 6/2004 |
| EP | 1 999 364 A1 | 12/2008 |
| FR | 2840920 A1 | 12/2003 |
| JP | 2007-525487 A | 9/2007 |
| WO | 00/29603 A2 | 5/2000 |
| WO | 2000026383 A1 | 5/2000 |
| WO | 2001/077313 A1 | 10/2001 |
| WO | 2002000879 A2 | 1/2002 |
| WO | 2006135075 A1 | 12/2006 |
| WO | 2007/101862 A1 | 9/2007 |
| WO | 2008/112092 A2 | 9/2008 |

OTHER PUBLICATIONS

International Search Report issued in Application No. PCT/EP2009/067531, dated Mar. 26, 2010.
Written Opinion of the International Searching Authority issued in application No. PCT/EP2009/067531, dated Mar. 26, 2010.
Y.M. Chen et al. "The Organization of the fuc Regulon Specifying L-Fucose Dissimilation in *Escherichia coli* K12 as Determined By Gene Cloning", Mol. Gen. Genet. 250:331-337. (1987).
Albermann C et al.: "Synthesis of the milk oligosachharide 2'-fucosyllactose using recombinant bacteial enzymes", Carbohydrate Research, Elsevier Scientific Publishing Company. Amsterdam, NL, vol. 334, No. 2, Aug. 23, 2001, pp. 97-103.
Coyne Michaet J et al.: "Human symboints use a host-like pathway for surface fucocylation" Science (Washington DC), vol. 307, No. 5716. Mar. 18, 2005 pp. 1778-1781.
Koizumi S. et al.: "Large-Scale Production of GDP-Fucose and LweisX by Bacterial Coupling", Journal of Industrial Microbriology and Boitechnology, Basingstoke, GB, vol. 25, No. 4, Oct. 1, 2000, pp. 213-217.
MA Bing et al.: "Fucosylation in prokaryotes and eurkaryotes" Glycobiology, Oxford University Pres, US, vol. 16, No. 12, Dec. 1, 2006, pp. 158R-184R.
Nimtz M. et al.: "In Vitro Alpha1-3 or Alpha1-4 Fucosylatin of type I and II Oligosaccharides with secreted forms of recombinant human fucosyltransfereases III and VI" vol. 15, Jan. 1, 1998, pp. 873-883.
Chinese Office Action issued in counterpart Chinese Application No. 200980151270 dated May 24, 2012.
Zhang et al., "Progess of Oligosacchardides Biosynthesis in recombinant *E. coli*," Chinese Journal of Biotechnology, vol. 23, No. 1, pp. 16-20.
Chinese Office Action with English Translation dated Oct. 25, 2013, issued in Chinese Application No. 200980151270.X.
Baldoma et al., "Metabolism of L-Fucose and L-Rhamnose in *Escherichia coli*: Aerobic-Anaerobic Regulation of L-Lactaldehyde Dissimilation", Journal of Bacteriology, vol. 170, No. 1, pp. 416-421. (1988).
European Communication dated Dec. 19, 2013, issued in corresponding European Application No. 09797036.2.
Sawa et al., "Glycoproteomic Probes for Flourescent Imaging of Fucosylated Glycans In Vivo", Proceedings of the National Academy of Sciences, vol. 103, No. 33, pp. 12371-12376. (Aug. 15, 2006).
Wang et al., "Chemoenzymatic Synthesis of GDP-L-Fucose and the Lewis X Glycan Derivatives", Proceedings of the National Academy of Sciences, vol. 106, No. 38, pp. 16096-16101. (Sep. 22, 2009).

(Continued)

*Primary Examiner* — Tekchand Saidha
(74) *Attorney, Agent, or Firm* — McNeill Baur PLLC

(57) ABSTRACT

A method for making a genetically modified cell having the ability to produce fucosylated compounds comprising the steps of: transforming the cell to express a fucose kinase, transforming the cell to express a fucose-1-phosphate guanylyltransferase, transforming the cell to express a fucosyltransferase.

5 Claims, 6 Drawing Sheets
Specification includes a Sequence Listing.

(56) References Cited

OTHER PUBLICATIONS

Russian Office Action (with English Translation) dated Oct. 23, 2013, issued in Russian Application No. 2011129780.
Hinderlich et al., "Identification of Human L-Fucose Kinase Amino Acid Sequence", Biochemical and Biophysical Research Communications, vol. 294, pp. 650-654. (2002).
Niittymäki et al., Cloning and Expression of Murine Enzymes Involved in the Salvage Pathway of GDP-L-Fucose, European Journal of Biochemistry, vol. 271, pp. 78-86. (2004).
Japanese Office Action issued in Japanese Application No. 2001-541476 dated Mar. 25, 2014. (English Translation).
Mexican Office Action issued in Mexican Application No. MX/a/2001/006371. (English Translation).
Andersson, B., 0. Porras, L. A. Hanson, T. Lagergard & C. Svanborg-Eden, (1986) Inhibition of attachment of *Streptococcus pneumoniae* and Haemophilus influenzae by human milk and receptor oligosaccharides. J Infect Dis 153: 232-237.
Appelmelk, B. J., M. C. Martino, E. Veenhof, M. A. Monteiro, 3. J. Maaskant, R. Negrini, F. Lindh, M. Perry, G. Del Giudice & C. M. Vandenbroucke-Grauls, (2000) Phase variation in H type I and Lewis a epitopes of Helicobacter pylori lipopolysaccha ride. Infect Immun 68: 5928-5932.
Appelmelk, B. J., S. L. Martin, M. A. Monteiro, C. A. Clayton, A. A. McColm, P. Zheng, T. Verboom, 3. J. Maaskant, D. H. van den Eijnden, C. H. Hokke, M. B. Perry, C. M. Vandenbroucke-Grauls & 3. G. Kusters, (1999) Phase variation in Helicobacter pylori lipopolysaccharide due to changes in the lengths of poly(C) tracts in alpha3-fucosyltransferase genes. Infect Immun 67: 5361-5366.
Bergman, M., G. Del Prete, Y. van Kooyk & B. Appelmelk, (2006) Helicobacter pylori phase variation, immune modulation and gastric autoimmunity. Nat Rev Microbiol 4: 151-159.
Bode, L., (2006) Recent advances on structure, metabolism, and function of human milk oligosaccharides. J Nutr 136: 2127-2130.
Coppa, G. V., L. Zampini, T. Galeazzi, B. Facinelli, L. Ferrante, R. Capretti & G. Orazio, (2006) Human milk oligosaccharides inhibit the adhesion to Caco-2 cells of diarrheal pathogens: *Escherichia co/i*, Vibrio choleraei and *Salmonella fyris*. Pediatr Res 59: 377-382.
Crane, J. K., S. S. Azar, A. Stam & D. S. Newburg, (1994) Oligosaccharides from human milk block binding and activity of the *Escherichia coli* heat-stable enterotoxin (STa) in T84 intestinal cells. J Nutr 124: 2358-2364.
Dravioto, A., A. Tello, H. Villafan, J. Ruiz, S. del Vedovo & J. R. Neeser, (1991) Inhibition of localized adhesion of enteropathogenic *Escherichia coli* to HEp-2 cells by immunoglobulin and oligosaccharide fractions of human colostrum and breast milk. J Infect Dis 163: 1247-1255.
Datsenko, K. A. & B. L. Wanner, (2000) One-step inactivation of chromosomal genes in *Escherichia coli* K-12 using PCR products. Proc Nati Acad Sci U S A 97: 6640-6645.
Dower, W. 3., J. F. Miller & C. W. Ragsdale, (1988) High efficiency transformation of *E. coli* by high voltage electroporation. Nucleic Acids Res 16: 6127-6145.
Dumon, C., B. Priem, S. L. Martin, A. Heyraud, C. Bosso & E. Samain, (2001) In vivo fucosylation of lacto-N-heotetraose and lacto-N-neohexaose by heterologous expression of Helicobacter pylori alpha-1,3 fucosyltransferase in engineered *Escherichia coli*. Glycoconj J 18:465-474.
Dumon, C., C. Bosso, 3. P. Utille, A. Heyraud & E. Samain, (2006) Production of Lewis x tetrasaccharides by metabolically engineered *Escherichia co/i* Chembiochem 7: 359-365.

Dumon, C., E. Samain & B. Priem, (2004) Assessment of the two Helicobacter pylori alpha-1,3-fucosyltransferase ortholog genes for the large-scale synthesis of LewisX human milk oligosaccharides by metabolically engineered *Escherichia coli*. Biotechnol Prog 20: 412-419.
Ge, Z., N. W. Chan, M. M. Palcic & D. E. Taylor, (1997) Cloning and heterologous expression of an alpha1,3-fucosyltransferase gene from the gastric pathogen Helicobacter pylori. J Biol Chem 272: 21357-21363.
Gnoth, M. J., S. Rudloff, C. Kunz & R. K. Kinne, (2001) Investigations of the in vitro transport of human milk oligosaccharides by a Caco-2 monolayer using a novel high performance liquid chromatography-mass spectrometry technique. J Biol Chem 276: 34363-34370.
Grant, W. D., I. W. Sutherland & J. F. Wilkimson, (1970) Control of colanic acid synthesis. J Bacteriol 103: 89-96.
Kretzschmar, G. & W. Stahl, (1998) Large scale synthesis of linker-modified sialyl-Lewis(X), Lewis(X) and N-acetyl-lactosamine. Tetrahedron 54: 6341-6358.
Kunz, C. & S. Rudloff, (2006) Health promoting aspects of milk oligosaccharides. Int Dairy J 16: 1341-1346.
Li, M., X. W. Liu, J. Shao, 1 Shen, Q. Jia, W. Yi, 1 K. Song, R. Woodward, C. S. Chow & P. G. Wang, (2008) Characterization of a novel alpha1,2-fucosyltransferase of *Escherichia coli* 0128:b12 and functional investigation of its common motif. Biochemistry 47: 378-387.
Martin, S. L., M. R. Edbrooke, T. C. Hodgman, D. H. van den Eijnden & M. I. Bird, (1997) Lewis X biosynthesis in Helicobacter pylori. Molecular cloning of an alpha(1,3)-fucosyltransferase gene. J Biol Chem 272: 21349-21356.
Newburg, D. S. & S. H. Neubauer, (1995) Carbohydrates in milk. In: Handbook of Milk Composition. R. G. Jensen (ed). San Diego, CA: Academic Press, pp. 273-349.
Newburg, D. S., (2001) Bioactive components of human milk: evolution, efficiency, and protection. Adv Exp Med Biol 501: 3-10.
Park, S.H., I. Pastuszak, R. Drake & A.D. Elbein, (1998). Purification to apparent homogenicity and properties of pig kidney L-fucose kinase. J Blot Chem 273: 5685-5691.
Rasko, D. A., G. Wang, M. M. Palcic & D. E. Taylor, (2000) Cloning and characterization of the alpha(1,3/4) fucosyltransferase of Helicobacter pylori. J Biol Chem 275: 4988-4994.
Ruiz-Palacios, G. M., L. E. Cervantes, P. Ramos, B. Chavez-Munguia & D. S. Newburg, (2003) Campylobacter jejuni binds intestinal H(0) antigen (Fuc alpha 1, 2Gal beta 1,4GlcNAc), and fucosyloligosaccharides of human milk inhibit its binding and infection. J Biol Chem 278: 14112-14120.
Stumpp, T., B. Wilms & J. Altenbuchner, (2000) Ein neues L-Rhamnose-induzierbares Expressionssystem fur *Escherichia coli*. BIOspektrum 6: 33-36.
Wang, G., D. A. Rasko, R. Sherburne & D. E. Taylor, (1999) Molecular genetic basis for the variable expression of Lewis Y antigen in Helicobacter pylori: analysis of the alpha (1,2) fucosyltransferase gene. Mol Microbiol 31: 1265-1274.
Wang, G., Z. Ge, D. A. Rasko & D. E. Taylor, (2000) Lewis antigens in Helicobacter pylori: biosynthesis and phase variation. Mol Microbiol 36: 1187-1196.
Office Action issued in Indian Patent Application No. 1050/MUMNP/2011, dated Jul. 13, 2017.
Lu, Z., et al., "The nucleotide sequence of *Escherichia coli* genes for L-fucose dissimilation," Nucleic Acids Research, vol. 17, No. 12, 1989, IRL Press, pp. 4883-4884.
Fleischmann, R.D., et al., "Whole-Genome Random Sequencing and Assembly of Haemophilus influenzae Rd," Research Article, Science, vol. 269, Jul. 28, 1995 (downloaded from www.sciencemag.org on Aug. 3, 2015), pp. 496-512.
ENZYME entry: EC 2.7.7.30, <http://enzyme.expasy.org/cgi-bin/enzyme/enzyme-search-ec,> retrieved May 8, 2013.

2'-Fucosyllactose  3-Fucosyllactose

SEQUENCE LISTING

```
<160> NUMBER OF SEQ ID NOS: 11

<210> SEQ ID NO 1
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaggaaacca tgggccaaaa actactatct ttaccgtcca atctggttca gtc           53

<210> SEQ ID NO 2
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggaaattg cggccgcatt atgatcgtga tacttggaat cccttatcag ataacg        56

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 3
aaggaataca tatgggaaac acatcaatac aaacgcagag ttaccgtgcg g          51

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaggaaactc gagtcagtta gttgccgttt gagaacggaa acgggcaaag           50

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagggaaacc atggctatgt tccagccgct gctggacgcg tttatcgagt ctgc      54

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagggaaagg atccgggtcc tattacagac ccagtttttt caccag              46

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggatctcgac gctctccct                                            19

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgcgtccgg cgtaga                                               16

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 9
gattatgcgg ccgtgtacaa                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgtacacgg ccgcataatc                                               20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatgctagtt attgctcag                                                19
```

SYNTHESIS OF FUCOSYLATED COMPOUNDS

This application is a divisional of U.S. application Ser. No. 13/140,548, filed Jun. 17, 2011, which is a National Stage Application of International Application No. PCT/EP2009/067531, filed Dec. 18, 2009, which claims priority to European Patent Application No. 08172267.0, filed Dec. 19, 2008, the entire contents of which are hereby incorporated by reference in their entirety.

SEQUENCE LISTING

The instant application contains a Sequence Listing which has been transferred from related U.S. patent application Ser. No. 13/140,548, filed on Jun. 17, 2011 and is hereby incorporated by reference in its entirety. Said Sequence Listing was previously submitted in ASCII format via EFS-WEB in said related application. Said ASCII copy was originally created on Aug. 15, 2011, is named "37998305.txt" and is 2,825 bytes in size.

The present invention is related to methods of making fucosylated compounds and cells related thereto.

Human milk consists of a complex mixture of carbohydrates, proteins, lipids, hormones, and micronutrients, providing all necessary nutrients for infant development. In addition human milk contains several protective agents. Besides immunoglobulins human milk contains an array of complex oligosaccharides with protective properties. Human milk oligosaccharide (HMO) fraction comprise beside the principal carbohydrate component lactose, more than 130 different complex oligosaccharides. This structural diversity of complex oligosaccharides and their occurrence at high amounts is unique to humans. In contrast, only trace amounts of much less complex oligosaccharides are found in bovine milk, and consequently commonly used infant formula lacks these oligosaccharides.

Clinical data showed that breast-fed infants have lower incidence of diarrhea, respiratory disease, and otitis media than formula-fed infants. For a long time these protective effects of human milk have been attributed to the presence of secreted immunoglobulins, however, it has now been recognized that the HMOs may be a major line of defense against pathogens for breast-fed infants. Many of the complex HMOs show homology to cell surface glycoconjugates such as the Lewis x ($Le^x$) histo-blood group antigen Gal (β1-4)[Fuc-(α1-3)]GlcNAc(β1) (Newburg, 2001), which often serve as pathogen receptors. Thus, by excreting soluble decoys, mimicking cell surface glycoconjugate structures, nature developed here an efficient mechanism to prevent infections. For example it was shown that HMOs can drastically reduce the virulence of pathogenic *Escherichia coli* (Cravioto et al., 1991), *Vibrio cholerae* (Coppa et al., 2006), *Streptococcus pneumoniae* (Andersson et al., 1986) or *Campylobacter jejuni* (Ruiz-Palacios et al., 2003) and are also able to neutralize toxins, like the heat-stable enterotoxin of *E. coli* (Crane et al., 1994). Besides the mentioned local effects in the intestinal tract, HMOs are also capable of eliciting systemic effects in infants by entering the systemic circulation (Gnoth et al., 2001).

The impact of HMOs on protein-carbohydrate interactions, e.g., selectin-leukocyte binding, can modulate immune responses and reduce inflammatory responses (Bode, 2006, Kunz & Rudloff, 2006).

Complex oligosaccharides represent the third largest component of human milk, after lactose and fat. They almost all have in common lactose at the reducing end, and are decorated with fucose and/or sialic acid at the non-reducing end. They are build from 3 to up to 32 monosaccharides and most of them contain fucose, with 1 to 15 fucose units. Thus, fucosylated oligosaccharides show great potential as bioactive food ingredients with anti-infective and prebiotic attributes.

Fucosyltransferases (FucTs), which catalyze the transfer of fucose residues from the donor guanosine-diphosphate activated L-fucose (GDP-L-fucose) to several acceptor molecules, are expressed in animals, plants, fungi and bacteria (Ma et al., 2006). They are categorized according to the site of fucose addition, therefore α1,2, α1,3/4, and α1,6 FucTs are distinguished. Besides human FucTs, which are originally responsible for the biosynthesis of HMOs and blood group antigens, several bacterial FucTs have been described. FucT activity has been best documented for the human gastric pathogen *Helicobacter pylori*, which decorates its lipopolysaccharide (LPS) with fucose-containing Lewis antigens (Wang et al., 2000). The exact role of these Lewis antigenic structures during *H. pylori* infection is unclear, but molecular mimicry to evade the host immune system, adhesion and colonization are discussed (Bergman et al., 2006).

Due to the great potential of HMOs as health-promoting food supplements, there is strong interest in the cost-effective large-scale production. Biocatalytic production via bacterial fermentation processes is highly favorable over extraction of HMOs from human milk, and chemical synthesis, which is laborious and requires multiple protection and deprotection steps (Kretzschmar & Stahl, 1998). During the last decade, several attempts of HMO synthesis using either fermentation with recombinant *E. coli* or in vitro enzymatic conversion, have been published (Albermann et al., 2001, Dumon et al., 2006, Dumon et al., 2001, Dumon et al., 2004, Koizumi et al., 2000). The bottleneck in the production of fucosylated oligosaccharides is, however, the availability of the donor nucleotide sugar GDP-fucose. This high-energy molecule is currently neither efficiently nor cost-effectively accessible via chemical or enzymatic synthesis. Most publications reporting production systems for fucosylated compounds rely on the endogenous GDP-fucose pool of *E. coli*, which however is extremely limited and only used for the inducible synthesis of the fucose-containing exopolysaccharide colanic acid (Grant et al., 1970).

For example Albermann et al. (2001) use recombinant enzymes in an enzymatic synthesis. GDP-ß-L-fucose is prepared by conversion of GDP-D-mannose to GDP-4-keto-6-deoxy-D-mannose. This is treated with a GDP-4-keto-6-deoxy-D-mannose 3,5 epimerase-4-reductase to produce GDP-ß-L-fucose, which is purified by preparative HPLC.

Another approach by Koizumi and co-workers to synthesize $Le^x$ from N-acetyllactosamine (LacNAc) involved the combination of GTP production from supplemented GMP by *Corynebacterium ammoniagenes*, GDP-fucose synthesis via GDP-mannose, and fucosylation of LacNAc by overexpression of a *H. pylori* α1,3-FucT in separate *E. coli* strains (Koizumi et al., 2000). Since permeabilization, and thus killing the cells, had to be used for this bacterial coupling approach, a continuous and large-scale fermentation process is not possible with this chosen approach.

There is still a need for methods for producing fucosylated compounds which overcome at least some of the drawbacks of prior art.

One embodiment of the invention is a method for making a genetically modified cell having the ability to produce fucosylated compounds comprising the steps of
- transforming the cell to express a fucose kinase
- transforming the cell to express a fucose-1-phosphate guanylyltransferase
- transforming the cell to express a fucosyltransferase.

According to the method of the invention a genetically modified cell is produced. It has been transformed to express a fucosekinase, a fucose-1-phosphate guanylyltransferase and a fucosyltransferase.

Methods of introducing genes into a cell are known to the skilled person.

In a preferred embodiment, the genetically modified cell is a microorganism selected from the group consisting of the genera *Escherichia, Klebsiella, Helicobacter, Bacillus, Lactobacillus, Streptococcus, Lactococcus, Pichia, Saccharomyces* and *Kluyveromyces*.

In a preferred embodiment of the invention, the fucose kinase and the fucose-1-phosphate guanylyltransferase activity are combined in a bifunctional enzyme. Suitable genes for transformation, coding for a fucose kinase, a fucose-1-phosphate guanylyltransferase and/or a bifunctional fucose kinase/fucose-1-phosphate guanylyltransferase can be obtained from the genera *Bacteroides, Lentisphaera, Ruminococcus, Solibacter, Arabidopsis, Oryza, Physcomitrella, Vitis, Danio, Bos, Equus, Macaca, Pan, Homo, Rattus, Mus* and *Xenopus*.

Suitable fucosyltransferase genes can be derived from organisms selected from the group of the genera *Helicobacter, Escherichia, Yersinia, Enterococcus, Shigella, Klebsiella, Salmonella, Bacteroides, Dictyostelium, Arabidopsis, Drosophila, Homo, Bos, Mus, Rattus, Gallus, Canis* and *Sus*.

Depending on the source of the gene and the cell used for expression, a codon optimization may be helpful to increase the expression.

Some cells have a catabolic pathway for fucose. In this case, it is recommendable to inactivate this catabolic pathway. Suitable methods comprise inactivating one or several genes selected from the group consisting of a fucose-1-phosphate aldolase gene, a fucose isomerase gene and a fuculose kinase gene.

Suitable fucose derived compounds which can be prepared by the genetically modified cells of the present invention are fucosyllactoses, preferably 2'-fucosyllactose, 3-fucosyllactose or lactodifucotetraose.

The present invention is a synthesis in a cell starting from fucose instead of a preparative synthesis with recombinant enzymes starting from GDP-D-mannose as described by Albermann et al. (2001).

A further embodiment of the invention is the genetically modified cell obtainable by the method of the invention. To produce fucosylated compounds, the genetically modified cell of the invention is cultivated under suitable cultivation conditions in a medium comprising fucose and an acceptor substrate.

Suitable acceptor substrates are for example a mono-, di- or oligosaccharide or a peptide, for example lactose, 2'-fucosyllactose or 3-fucosyllactose.

The preferred fucosylated compounds obtained by the production method are fucosyllactoses, preferably 2'-fucosyllactose or 3-fucosyllactose or lactodifucotetraose.

This is the first report of efficient GDP-fucose synthesis in *E. coli* from externally supplied L-fucose and thus the establishment of an fucose "salvage pathway" in *E. coli*. However, this approach may also be transferred to other easy to culture organisms of interest to food or pharmaceutical industry (for example *Lactobacillus* spp.). Usage of this newly discovered pathway offers utterly new perspective for production of oligosaccharides, besides 2'-fucosyllactose and 3-fucosyllactose, without the need to rely on costly and laborious provision of GDP-fucose (in vitro) or endogenous, highly regulated, GDP-fucose biosynthetic pathways (in vivo).

In the so called "fucose salvage pathway" fucose is first phosphorylated to fucose-1-phosphate by the enzyme fucose kinase. The fucose-1-phosphate is then converted to GDP-fucose by the action of the enzyme fucose-1-P-guanylyltransferase. Recently, the first bacterial enzyme, Fkp, with both fucose kinase and L-fucose-1-P-guanylyltransferase activity was described (Coyne et al., 2005). The intestinal bacterium *Bacteroides fragilis* uses the enzyme for the production of GDP-fucose, which serves for the decoration of capsular polysaccharides and glycoproteins with fucose residues.

EXAMPLES

Figure 1:
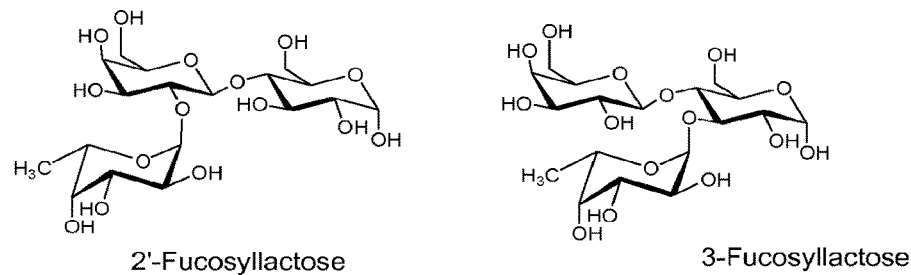
FIG. 1 discloses the structures of the prominent complex human milk oligosaccharides (HMOs) 2'-fucosyllactose and 3-fucosyllactose.

This invention is further explained by the following, non-limiting examples:

Example 1

Construction of Expression Plasmids and Development of Production Strains

To successfully prevent the degradation of externally supplied fucose the fucA gene, coding for the key catabolic enzyme fuculose-1-phosphate aldolase had to be deleted from the genome of *E. coli* strain BW25113. For construction of the fucA deletion the methodology of (Datsenko & Wanner, 2000) was applied. For heterologous gene expression using the T7 promoter an inducible T7 RNA polymerase was incorporated into the deletion strain *E. coli* BW25113 ΔfucA by using the λDE3 lysogenization kit (Novagen). The resulting strain was then named *E. coli* BW25113 ΔfucA (DE3). The plasmids pCOLA-fkp-fucP and pET-futAco were constructed using the pCOLADuet-1 and pETDuet-1 expression vectors (Novagen). All primers used for the construction are listed in Table 2. Gene fkp (GeneBank acc. no. AY849806) was amplified by PCR with primers fkp-NcoI-forward and fkp-NotI-reverse using genomic DNA of *Bacteroides fragilis* ATCC 25285D. The fucP gene (GeneBank acc. no. CP000948) of *Escherichia coli* K12 was amplified from genomic DNA of *E. coli* TOP10 (Invitrogen, USA) using primers FucP-NdeI-forward and FucP-XhoI-reverse. Both fkp and fucP were inserted into the first and second multiple cloning site (MCS) of pCOLADuet-1, respectively, using the indicated restriction sites. The resulting plasmid was designated pCOLA-fkp-fucP. The futA gene (GeneBank acc. no. AE000511) of *H. pylori* strain 26695 was codon-optimized for expression in *E. coli* and prepared synthetically by GenScript Corporation (Piscataway, N.J., USA). The gene was amplified using the primers FutAco-NcoI-forward and FutAco-BamHI-reverse, and inserted into the first MCS of pETDuet-1, yielding pET-futAco. The correct insertion of cloned genes was checked by restriction analysis and sequencing using the recommended primers pACYCDuetUP1, pET-Upstream, DuetDOWN-1, DuetUP2 and T7-Terminator listed in the Duet Vectors Manual (Novagen). Plasmid pCAW55 containing the gene fucT2 coding for α1,2-fucosyltransferase from *Helicobacter pylori* NCTC364 was donated by C. Albermann (Institute for Microbiology, University of Stuttgart) and is based on vector pJOE2702 (Stumpp et al., 2000). Gene fucT2 is inserted via restriction sites NdeI/PstI and controlled by L-rhamnose-inducible promoter rhaPBAD. *E. coli* BW25113 ΔfucA (DE3) was transformed with the expression vectors by electroporation (Dower et al., 1988). All bacterial strains used in this study are listed in Table 1.

TABLE 1

Bacterial strains and plasmids used.

| Name | Relevant characteristic(s)* | References |
|---|---|---|
| *E. coli* strains | | |
| BW25113 | Δ(araD-araB)567, ΔlacZ4787(::rrnB-3), lambda⁻, rph-1, Δ(rhaD-rhaB)568, hsdR514 | (Datsenko & Wanner, 2000) |
| BW25113ΔfucA (DE3) | BW25113 fucA mutant, carrying chromosomal copy of λDE3 T7 RNA polymerase gene | This study |
| BW25113ΔfucA (DE3) pCOLADuet-1 pETDuet-1 | Negative control strain harboring empty vectors, Ap$^R$, Kan$^R$ | This study |
| BW25113ΔfucA (DE3) pCOLA-fkp-fucP | Km$^R$ | This study |
| BW25113ΔfucA (DE3) pCOLA-fkp-fucP pET-futAco | Ap$^R$, Km$^R$ | This study |
| BW25113ΔfucA (DE3) pCOLA-fkp-fucP pCAW55 | Ap$^R$, Km$^R$ | This study |
| Plasmids | | |
| pCOLADuet-1 | Km$^R$ | Novagen |
| pETDuet-1 | Ap$^R$ | Novagen |
| pCOLA-fkp-fucP | Km$^R$ | This study |
| pET-futAco | Ap$^R$ | This study |
| pCAW55 | Ap$^R$ | C. Albermann |

*Ap$^R$, ampicillin resistant, Km$^R$, kanamycin resistant.

TABLE 2

Primers.

| Name | Sequence (5' → 3')* | Added restriction site |
|---|---|---|
| Fkp-NcoI-forward | AAGGAAA<u>CCATGG</u>GCCAAAAACTACTATCTTTACCG TCCAATCTGGTTCAGTC | NcoI |
| Fkp-NotI-reverse | AAGGAAATT<u>GCGGCCGC</u>ATTATGATCGTGATACTTG GAATCCCTTATCAGATAACG | NotI |
| FucP-NdeI-forward | AAGGAATA<u>CATATG</u>GGAAACACATCAATACAAACGC AGAGTTACCGTGCGG | NdeI |
| FucP-XhoI-reverse | AAGGAAA<u>CTCGAG</u>TCAGTTAGTTGCCGTTTGAGAAC GGAAACGGGCAAAG | XhoI |
| FutAco-NcoI-forward | AAGGGAAA<u>CCATGG</u>CTATGTTCCAGCCGCTGCTGG ACGCGTTTATCGAGTCTGC | NcoI |
| FutAco-BamHI-reverse | AAGGGAAA<u>GGATCC</u>GGGTCCTATTACAGACCCAGT TTTTTCACCAG | BamHI |
| pACYCDuetUP1 | GGATCTCGACGCTCTCCCT | |
| pET-Upstream-Primer | ATGCGTCCGGCGTAGA | |
| DuetDOWN-1-Primer | GATTATGCGGCCGTGTACAA | |
| DuetUP2-Primer | TTGTACACGGCCGCATAATC | |
| T7-Terminator-Primer | TATGCTAGTTATTGCTCAG | |

*The restriction endonuclease recognition sites are underlined.

Example 2

Cultivation Conditions and Preparation of Cell Extracts

E. coli strains were inoculated in 10 mL of 2×YT broth (Sambrook & Russell, 2001), containing 100 μg mL$^{-1}$ ampicillin and/or 50 μg mL$^{-1}$ kanamycin, and incubated overnight in a rotary shaker at 37° C. The next day, 30 mL fresh 2×YT broth supplemented with the appropriate antibiotics was inoculated 1/100 from the overnight culture, and incubated at 37° C. in a rotary shaker providing good aeration. When the cultures reached an optical density (OD$_{600}$ nm) of approximately 0.5, inducers isopropyl-1-thio-3β-D-galactopyranoside (IPTG) and/or L-rhamnose were added in a concentration of 0.1 mM and 0.1%, respectively. The cultures were further incubated at 28° C. overnight (approx. 15 h) under constant shaking. For photometric activity assay an aliquot of cell culture was removed, cells were pelleted and resuspended in five times weight/volume 50 mM Tris-HCl pH 7.5. Glass beads were added four times the weight of cell pellet and the resulting suspension was vortexed two times for five minutes each and in between placed on ice for additional five minutes. Cell debris was removed by centrifugation (13200 rpm, 5 min, 4° C.) and the resulting crude extract was stored at 4° C.

For in vivo production of fucosyllactose, cells were washed with one culture volume of phosphate buffered saline pH 7.4 (PBS) (Sambrook & Russell, 2001), and resuspended in 30 mL of modified M9 mineral medium; to the standard M9 recipe (Sambrook & Russell, 2001), the following substances were added: 20 mM L-fucose, 20 mM lactose, 0.5% glycerol, 0.5 mM guanosine and 1×GIBCO MEM Vitamin Solution (100×) (Invitrogen, USA). Inducers L-rhamnose (0.1%) and IPTG (0.1 mM) were also added to all cultures regardless of which strain was cultivated to avoid different culture conditions. Again, the cultures were incubated at 28° C. overnight (approx. 15 h) under constant shaking. The cultures were centrifuged and the supernatants were decanted and stored at −20° C. The cells were subsequently washed with PBS, resuspended in distilled water, and permeabilized by autoclaving (100° C., 5 min). To remove cell debris, the samples were centrifuged (8500 rpm, 30 min) and the clear cell lysate was stored at −20° C.

Example 3

SDS-PAGE

The expression of heterologous proteins was checked by SDS-PAGE (Sambrook & Russell, 2001). Protein extracts were prepared in 1×SDS gel-loading buffer, and polyacrylamide gels were stained with Coomassie Brilliant Blue.

Example 4

Enzymatic Photometer Assays

Example 4a

Figure 2:
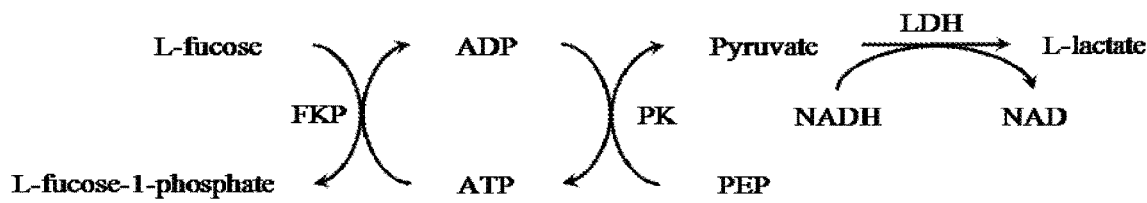
FIG. 2 shows a scheme of the photometric assay for determination of Fkp activity by coupled enzyme reactions and determination of NADH oxidation; Fkp=bifunctional fucose kinase/fucose-1-phosphate guanylyltransferase, PK=pyruvate kinase, LDH=L-lactate dehydrogenase, PEP=phosphoenolpyruvate.

To determine Fkp activity, fucose kinase activity of the enzyme was measured by the amount of arising ADP from ATP, used as a substrate by pyruvate kinase (PK) while dephosphorylating phosphoenolpyruvate (PEP), whereas the resulting pyruvate was then converted to L-lactate by L-lactate dehydrogenase (LDH) under NADH consumption. The corresponding reactions are summarized in FIG. 2. Each 1000 μL reaction was performed in 65 mM MOPS buffer (pH 7.5) containing 10 mM L-fucose, 15 mM PEP, 5 mM MgSO$_4$, 0.2 mM of each ATP and NADH, and 5 U of each PK and LDH. After the addition of 25 μL crude extract, the oxidation of NADH to NAD was monitored via the decrease of absorption at 340 nm using a V-630 Bio spectrophotometer (JASCO GmbH, Germany).

Example 4b

Figure 3:
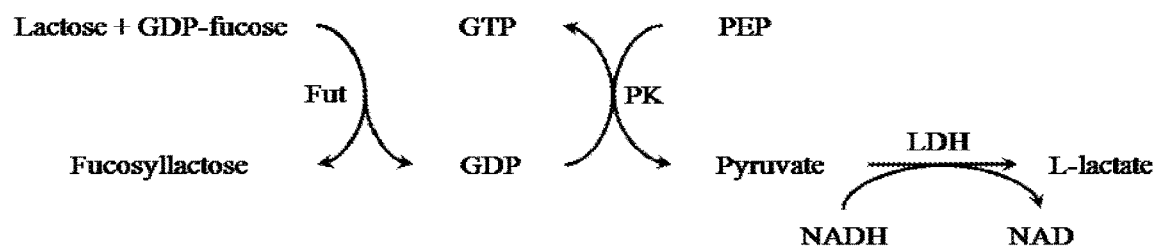
FIG. 3 shows a scheme of the photometric assay for determination of FucT activity by coupled enzyme reactions and determination of NADH oxidation; FucT=fucosyltransferase, PK=pyruvate kinase, LDH=L-lactate dehydrogenase, PEP=phosphoenolpyruvate.

Analogously, FucT activity was (as shown in FIG. 3) measured by arising GDP (from the donor GDP-L-fucose) which was phosphorylated to GTP by PK under conversion of PEP to pyruvate. LDH catalyzed the final reaction of pyruvate reduction to L-lactate with concomitant NADH consumption. Cellular extracts (25 µL) were tested in a 1000 µL reaction containing 10 mM lactose, 100 µM GDP-L-fucose, 5 mM $MgSO_4$, 0.2 mM of each ATP and NADH, and 5 U of each PK and LDH in 50 mM Tris-HCl buffer (pH 7.5). The decrease of NADH was monitored at 340 nm.

Example 5

Detection of Oligosaccharides

Samples were analyzed by high performance anion exchange chromatography (HPAED) using a Decade II pulsed amperometric detector from Antec Leyden (Netherlands) and a CarboPac PA20 column (Dionex, Germany) connected to a HPLC system (Shimadzu, Germany). The detector sensitivity was set at 50 µA with a 0.05-V applied pulse potential. Mono-, di-, and oligosaccharides eluted with 10 mM sodium hydroxide at a flow rate of 0.4 mL min$^{-1}$. After 30 min isocratic elution with 10 mM NaOH the column was washed for 20 min with 200 mM NaOH to obtain constant retention times and thereafter regenerated with 10 mM NaOH for 20 min.

Example 6

$^3$H-Fucose Feeding Experiments

E. coli BW25113 ΔfucA (DE3) cells were transformed with the vectors pCOLADuet-1, pETDuet-1, pCOLA-fkp-fucP and pET-futAco to generate the following strains:
E. coli BW25113 ΔfucA (DE3) pCOLADuet-1 pETDuet-1
E. coli BW25113 ΔfucA (DE3) pCOLA-fkp-fucP
E. coli BW25113 ΔfucA (DE3) pCOLA-fkp-fucP pET-futAco.

Strain E. coli BW25113 ΔfucA (DE3) pCOLADuet-1 pETDuet-1 served as empty vector control in the feeding experiments. All three strains were then used for tritium labeled fucose feeding experiments. For the feeding experiments cells were cultured in 3 ml of 2×YT medium containing 20 µl L-5,6-$^3$H-Fucose (40-60 Ci/mmol and 1 mCi/mL), 50 mM lactose and 1 mM IPTG. According to the used expression vectors 2×YT medium was supplemented with 100 µg mL$^{-1}$ ampicillin and/or 50 µg mL$^{-1}$ kanamycin. The 3 mL E. coli cultures were incubated at room temperature overnight. Cells were then collected by centrifugation and separated from the culture media, the obtained cell pellets were resuspended in 200 µL of dd$H_2O$ and boiled for 5 min. After cooling on ice for 10 min cell debris were collected by centrifugation at 13000 rpm for 10 min. From the so obtained E. coli cell supernatants 20 µL of each culture were applied to a silica gel TLC plate (Silica gel 60). For the development of the TLC plate a solvent mixture consisting of butanol:acetone:acetic acid:water (35:35:7:23) was employed. Radio-TLC analysis was then performed with a Radio-TLC reader (Raytest). For the determination of Rf-values of non-radioactive reference material the TLC plate was sprayed with anisaldehyde solution (5 mL conc. $H_2SO_4$, 100 mL ethanol, 1.5 mL acetic acid, 2 mL anisaldehyde) and heated.

Example 7

Establishment of an Efficient L-Fucose Salvage Pathway in E. coli

Since lactose was used as acceptor substrate for the fucosyltransferases, the 3-galactosidase deficient (lacZ$^-$) E. coli strain BW25113 was chosen to circumvent the problem of rapid lactose degradation (Datsenko & Wanner, 2000). L-Fucose can be also effectively degraded by wild type E. coli via isomerization to fuculose, phosphorylation to fuculose-1-phosphate and subsequent retro-aldol cleavage of fuculose-1-phosphate to glycerin-3-phosphate and L-lactaldehyde. To prevent degradation of supplied fucose the gene fucA, encoding the key catabolic enzyme of the fucose degradation pathway fuculose-1-phosphate aldolase (FucA), was deleted in the genome of strain E. coli BW25113. The resulting strain E. coli BW25113 ΔfucA was unable to grow on fucose as well as lactose as sole carbon source on M9 minimal plates. Lysogenization with recombinant phage λDE3 resulted in strain E. coli BW25113 ΔfucA (DE3) compatible with the use of T7 promoter driven expression vectors. The ability of nucleotide activation of fucose to GDP-fucose is very limited in nature and was also for a long time only known from several mammals (human, pig, mouse). Nucleotide activation of fucose is mediated here by two successive enzymatic steps, first the phosphorylation of fucose to fucose-1-phosphate, catalyzed by fucose kinase and followed by the conversion of fucose-1-phosphate to GDP-Fucose, catalyzed by guanylyltransferase, respectively. Whereas in mammals the fucose salvage pathway comprises two separate enzyme catalyzed reactions, the recently discovered bacterial and plant proteins comprise both enzymatic activities. Heterologous expression of human fucose kinase in E. coli resulted only in barely detectable activity (Hinderlich et al., 2002). Biochemical studies showed that mammalian fucokinase represents a highly regulated enzyme (Park et al., 1998). To examine of whether the recently discovered B. fragilis Fkp enzyme is more suitable for activation of fucose and to efficiently provide GDP-fucose for the synthesis of fucosylated oligosaccharides in E. coli we amplified the gene from B. fragilis genomic DNA and cloned it into a bacterial expression vector for heterologous expression.

Figure 4:
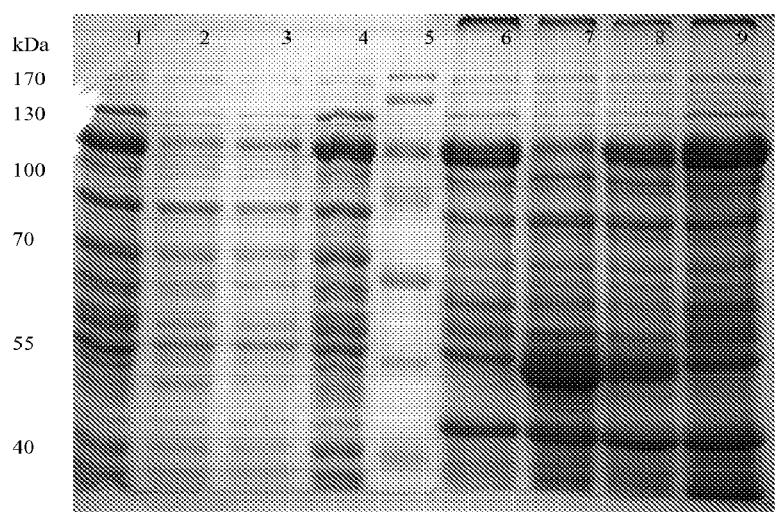
FIG. 4 shows the protein formation after induction. Lanes 1-4: expression of soluble Fkp (105.7 kDa) and/or FutAco (49.3 kDa) or FucT2 (35.9 kDa), in crude extracts from *E. coli* BW25113 ΔfucA (DE3) pCOLA-fkp-fucP (lane 1), *E. coli* BW25113 ΔfucA (DE3) pET-futAco (lane 2), *E. coli* BW25113 ΔfucA (DE3) pCOLA-fkp-fucP+pETfutAco (lane 3) and *E. coli* BW25113 ΔfucA (DE3) pCOLA-fkp-fucP+pCAW55 (lane 4); lane 5: PageRuler™ Prestained Protein Ladder (Fermentas, Germany); lanes 6-9: expression of insoluble Fkp and/or FutAco or FucT2, in cell debris resuspended in 6 M urea from *E. coli* BW25113 ΔfucA (DE3) pCOLA-fkp-fucP (lane 6), *E. coli* BW25113 ΔfucA (DE3) pET-futAco (lane 7), *E. coli* BW25113 ΔfucA (DE3) pCOLA-fkp-fucP+pETfutAco (lane 8) and *E. coli* BW25113 ΔfucA (DE3) pCOLA-fkp-fucP+pCAW55 (lane 9).

For the synthesis of 2'- and 3-fucosyllactose the following fucosyltransferases were chosen for co-expression: The futA gene of H. pylori 26695 (Appelmelk et al., 1999), encoding an α1,3-fucosyltransferase, and the α1,2'-fucosyltransferase gene fucT2 of H. pylori NCTC364 (Albermann et al., 2001). Before the start of the cloning process, the codon usage of futA was optimized for expression in E. coli and the gene was then synthesized by GenScript corporation (USA). The resulting gene futAco was inserted in the expression vector pETDuet-1, and expression was tested with and without co-expression of Fkp and FucP. Using standard induction conditions, Fkp, FucP and FutAco or FucT2 were co-expressed. Protein formation was examined after induction with IPTG and/or L-rhamnose with SDS-PAGE (see FIG. 4), documenting pronounced soluble production of Fkp protein, whereas induction of membrane localized fucose permease protein (FucP) could, as expected, not be detected in cell cytoplasm by SDS-PAGE. However, the gene products of futAco and fucT2 proved to be primarily located in inclusion bodies with only a small soluble fraction detectable.

Example 8

Photometric Detection of Enzymatic Activity

The crude extracts derived from induced cultures were tested for fucose kinase and fucosyltransferase activity using auxiliary enzymes in coupled enzymatic assays as described above. Apparently, there is a considerable background of either NADH oxidase and/or phosphatase activity in E. coli BW25113 ΔfucA (DE3), which was responsible for non-reproducible results and low measured fucose kinase and fucosyltransferase activity of the different strains. Therefore, it was decided to determine enzymatic activity by monitoring intracellular product formation (GDP-fucose and fucosyllactose).

Example 9

Figure 5:
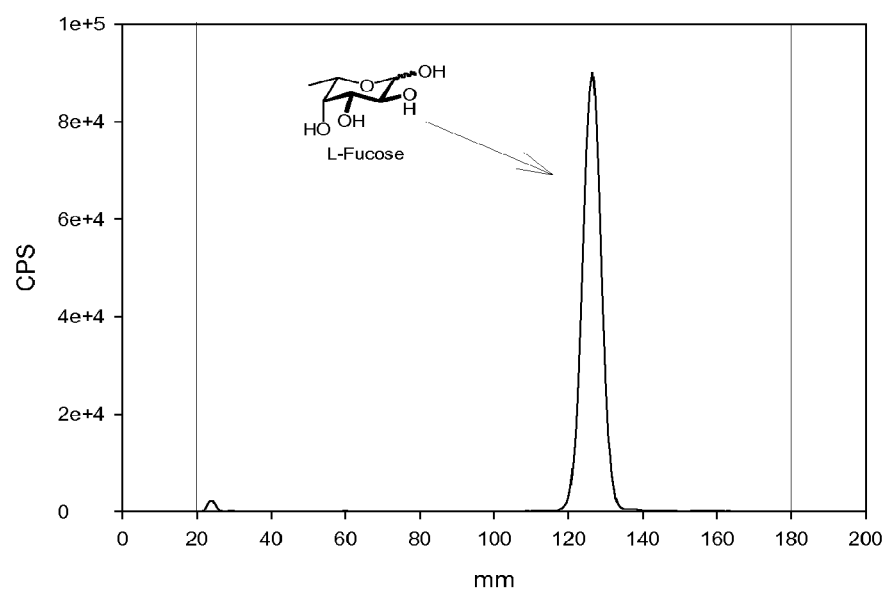
FIG. 5 shows a radio thin layer chromatography (radio-TLC) of $^3$H-fucose, developed with butanol:acetone:acetic acid:water (35:35:7:23) and analyzed using a radio-TLC reader.

Examination of Utilization of Externally Fed $^3$H-L-Fucose for GDP-Fucose and 3-Fucosyllactose Production by Recombinant E. coli The aim of this experiment was the verification of 3-fucosyllactose production from fucose and lactose via GDP-fucose production by the fucose salvage pathway bifunctional enzyme Fkp from Bacteroides fragilis. Negative control strain E. coli BW25113 ΔfucA (DE3) pCOLADuet-1 pETDuet-1, as well as Fkp and fucose permease expressing strain E. coli BW25113 ΔfucA (DE3) pCOLA-fkp-fucP and Fkp, fucose-permease and α1,3-fucosyltransferase expressing strain E. coli BW25113 ΔfucA (DE3) pCOLA-fkp-fucP pET-futAco were treated as described above. Cell extracts derived from these strains were applied to a TLC plate, developed as described above and analyzed by radio-TLC reader. Additionally, $^3$H-labelled L-fucose standard was applied to a TLC plate and developed (see FIG. 5). Non-radioactive standards for L-fucose and L-fuculose-1-phosphate, GDP-L-fucose, as well as 3-fucosyllactose were analyzed similarly by TLC and subsequent staining by anisaldehyde solution (data not shown).

Figure 6:
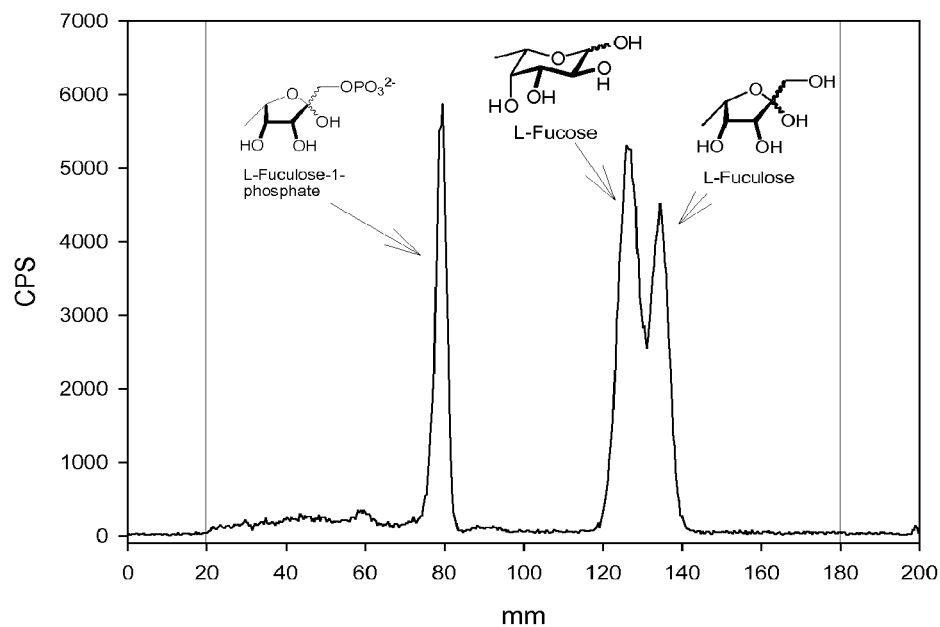
FIG. 6 shows a radio-TLC of a cell extract from *E. coli* BW25113 ΔfucA (DE3) pCOLADuet-1 pETDuet-1 showing fucose and fuculose and fuculose-1-phosphate, however degradation of fuculose-1-phosphate is inhibited due to the genomic knockout of the fuculose-1-phosphate aldolase gene (fucA).

The results of the negative control experiment (see FIG. 6) showed products of the first and second catabolic steps from the fucose metabolism, i.e. L-fuculose (produced from fucose by fucose isomerase) and L-fuculose-1-phosphate (produced from fuculose by fuculose kinase). Further degradation of fucose is effectively inhibited by the knock-out of the gene fucA, which encodes the enzyme fuculose-1-phosphate aldolase, which catalyzes the retro-aldol cleavage reaction of fuculose-1-phosphate to L-lactaldehyde and dihydroxyacetone phosphate.

Figure 7:
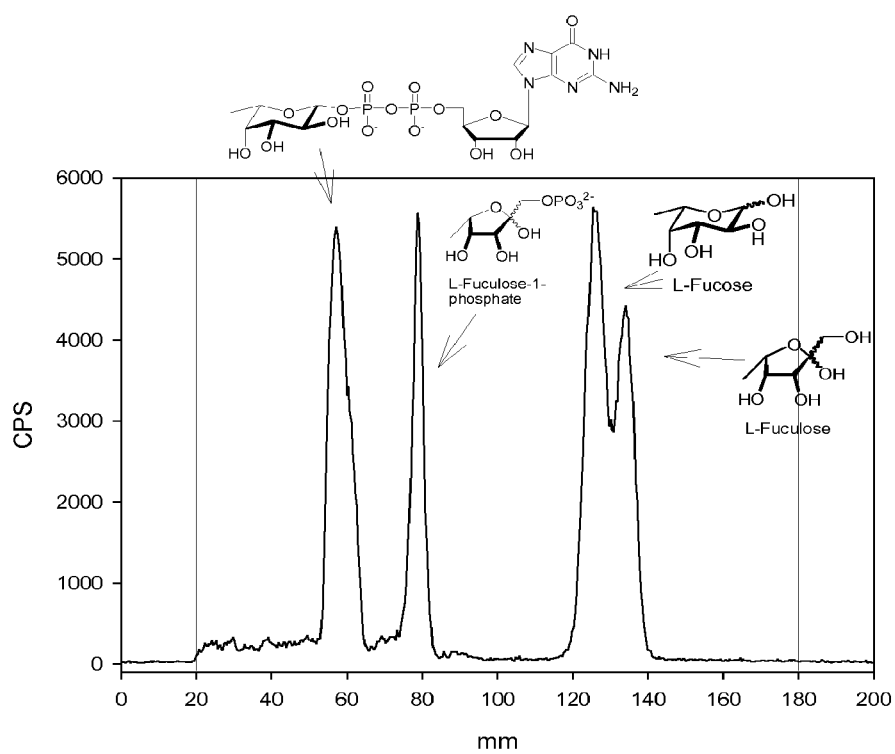
FIG. 7 shows radio-TLC of cell extract from *E. coli* BW25113 ΔfucA (DE3) pCOLA-fkp-fucP showing accumulating GDP-fucose produced by bifunctional fucose kinase/fucose-1-phosphate guanylyltransferase Fkp from *Bacteroides fragilis* as well as fucose and degradation products fuculose and fuculose-1-phosphate.

E. coli cells coexpressing bifunctional fucose kinase/fucose-1-phosphate guanylyltransferase Fkp from Bacteroides fragilis show the production of GDP-fucose (see FIG. 7) which is apparently accumulating in the cells and may only minimally divert into other metabolic pathways whose products would otherwise appear on the radio-TLC.

Figure 8:
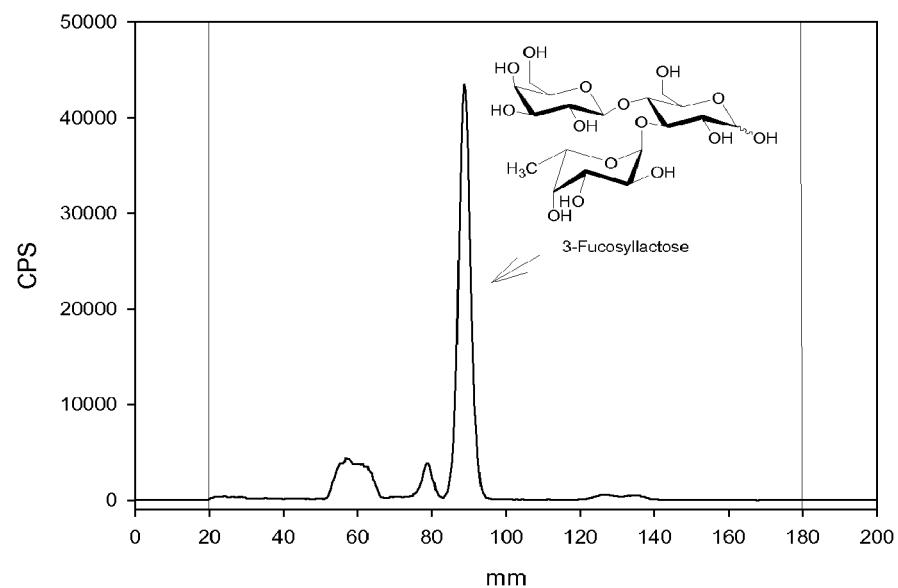
FIG. 8 shows a radio-TLC of a cell extract from *E. coli* BW25113 ΔfucA (DE3) pCOLA-fkp-fucP pET-futAco showing accumulating 3-fucosyllactose produced by codon optimized fucosyltransferase of *Helicobacter pylori* via GDP-fucose provided by bifunctional fucose kinase/fucose-1-phosphate guanylyltransferase (Fkp). Fucose and degradation products fuculose and fuculose-1-phosphate are only minimally present; GDP-fucose amount is significantly reduced due to 3-fucosyllactose production.

Cell extracts from strain E. coli BW25113 ΔfucA (DE3) pCOLA-fkp-fucP pET-futAco show production of 3-fucosyllactose and only a small amount of GDP-fucose (see FIG. 8). This result is consistent with the initial aim of the experiment, i.e. to show the production of 3-fucosyllactose via GDP-fucose supply by bifunctional salvage pathway enzyme Fkp from Bacteroides fragilis. The amount of fucose degradation products fuculose and fuculose-1-phosphate is also greatly diminished, due to the consumption of GDP-fucose in fucosyllactose production and the deriving drift of the reaction equilibrium from fuculose-1-phosphate and fuculose to fucose, which is constantly drawn from the reaction by GDP-fucose production.

Example 10

Examination of 2'-Fucosyllactose and 3-Fucosyllactose Production by Recombinant E. coli Strain E. coli BW25113 ΔfucA (DE3) harboring pCOLA-fkp-fucP and either the futAco or fucT2 gene in a separate expression vector, as well as E. coli BW25113 ΔfucA (DE3) harboring the empty vectors pCOLADuet-1 and pETDuet-1 (negative control) were grown in 2×YT broth, and protein expression was induced with IPTG and/or L-rhamnose for 15 h at 28° C. The cells were subsequently washed with PBS and resuspended in modified M9 medium supplemented with L-fucose, lactose and guanosine, IPTG and L-rhamnose. After a fermentation phase (28° C., 15 h), the cells were harvested, supernatants collected and cell lysates prepared as described above.

Analysis via HPAED showed retention times on the used HPLC column of approximately 3 min for the L-fucose standard, approx. 17 min for the lactose standard, approx. 11 min for the 3-fucosyllactose standard, and of approx. 22 min for the used 2'-fucosyllactose standard (data not shown). Glycerol, that is, as carbon source, part of the culture medium, was recorded with a retention time of approx. 1.5 min, and inducer L-rhamnose with a retention time of 5.5 min. Both substances are detected intracellularly during analysis of cell lysates.

Figure 9:
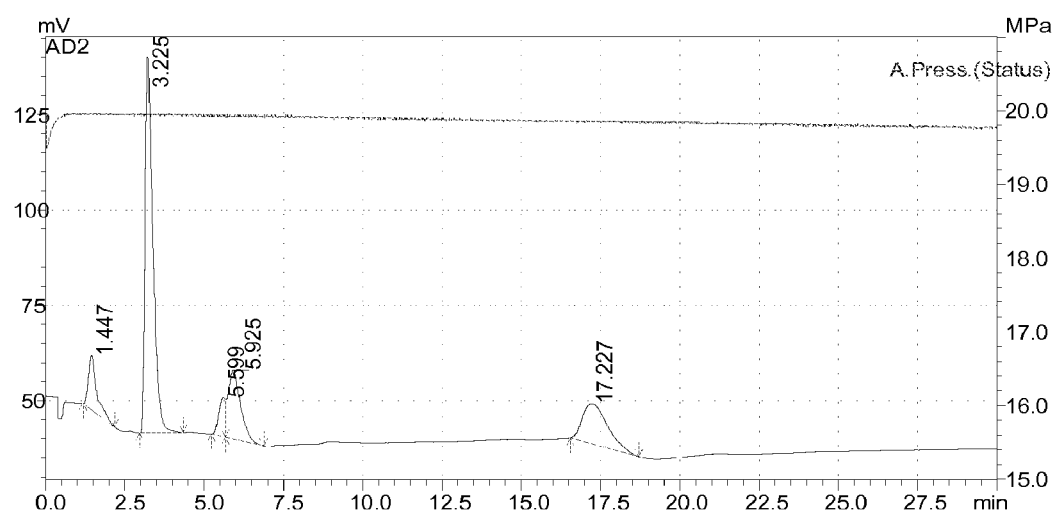
FIG. 9 shows a HPAED analysis of cell lysate from negative control strain *E. coli* BW25113 ΔfucA (DE3) pCOLADuet-1 pETDuet-1 showing intracellular L-fucose, lactose, glycerol and L-rhamnose, but no fucosyllactose.

Cell lysates from E. coli BW25113 ΔfucA (DE3) pCOLADuet-1 pETDuet-1 negative control strain showed intracellular L-fucose and lactose, but, as expected, no fucosyllactose (see FIG. 9). In addition to the aforementioned molecules also the medium supplied carbon source glycerol and the transcription inducer L-rhamnose are detected in the analysis.

Figure 10:
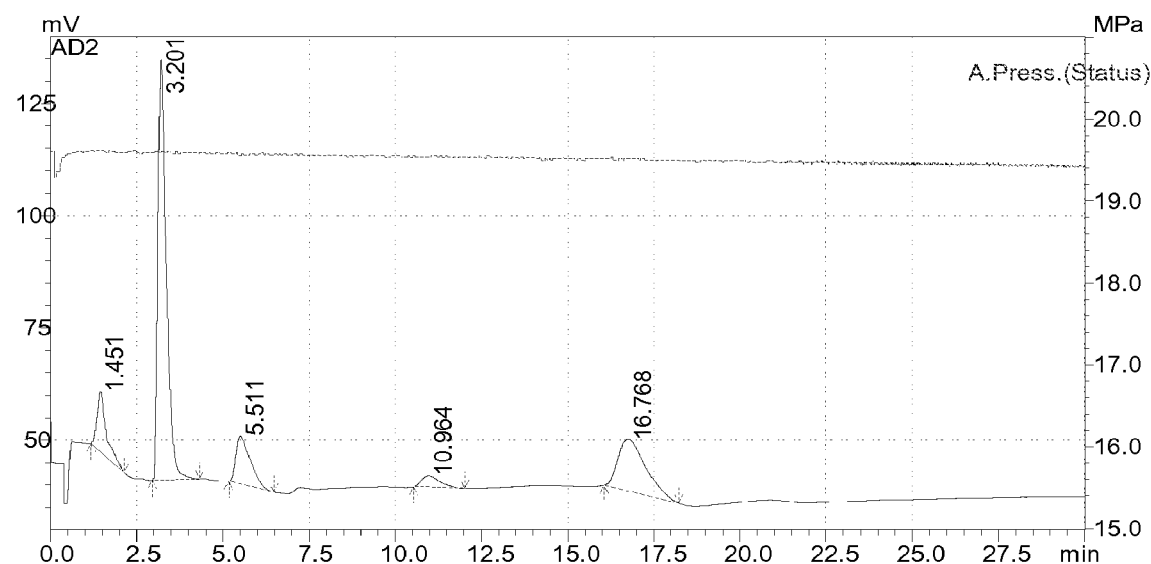
FIG. 10 shows a cell lysate of strain *E. coli* BW25113 ΔfucA (DE3) pCOLA-fkp-fucP pET-futAco producing 3-fucosyllactose (retention time of about 11 min); furthermore L-fucose, lactose, glycerol and L-rhamnose peaks can be seen.

HPAED analysis of cell lysate from strain E. coli BW25113 ΔfucA (DE3) pCOLA-fkp-fucP pET-futAco, coexpressing the B. fragilis fkp gene and E. coli fucose permease gene in combination with the codon optimized Helicobacter pylori α1,3-fucosyltransferase gene, showed the intracellular production of 3-fucosyllactose (peak at about 11 min, see FIG. 10). L-fucose and lactose are also components of the cell lysate, as well as glycerol and L-rhamnose.

Figure 11:
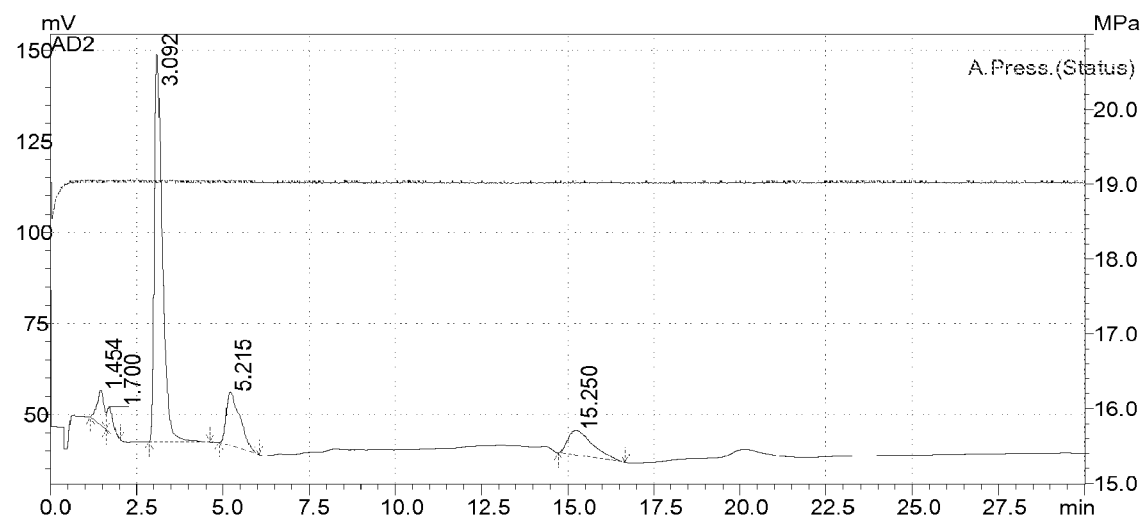
FIG. 11 shows a HPAED analysis of cell lysate from strain *E. coli* BW25113 ΔfucA (DE3) pCOLA-fkp-fucP pCAW55 showed production of 2'-fucosyllactose (retention time of about 22 min). Additionally, L-fucose, lactose, glycerol and L-rhamnose can be seen.

Cell lysate from strain E. coli BW25113 ΔfucA (DE3) pCOLA-fkp-fucP pCAW55 showed intracellular production of 2'-fucosyllactose (see FIG. 11), due to the coexpression of α1,2-fucosyltransferase FucT2. Additionally, L-fucose, lactose, glycerol and L-rhamnose can be seen in cell lysate, just as in cell lysate from negative control and 3-fucosyllactose producing strain E. coli BW25113 ΔfucA (DE3) pCOLA-fkp-fucP pET-futAco.

These results clearly show the production of 3- and 2'-fucosyllactose in recombinant E. coli cells from externally supplied L-fucose and lactose. By heterologous expression of B. fragilis Fkp protein, catalyzing the two-step reaction of fucose phosphorylation and fucose-1-phosphate guanylyl transfer, efficient production of GDP-fucose was obtained. Codon optimized α1,3-fucosyltransferase FutAco initially derived from Helicobacter pylori or α1,2-fucosyltransferase FucT2 from Helicobacter pylori, respectively, can convert the so supplied GDP-fucose into 2'- and 3-fucosyllactose.

Example 11

Expression of GDP-Fucose in *E. coli* JM109 Cells

Elevation of intracellular GDP-fucose content due to expression of Fkp was shown by parallel cultivation of an *E. coli* strain expressing Fkp from a plasmid and an *E. coli* strain not containing a copy of Fkp. Strain *E. coli* JM109 (DE3) ΔfucA was in this case used as control strain without Fkp. The strain expressing Fkp was the same strain *E. coli* JM109 (DE3) ΔfucA, this time containing the plasmid pCOLA-fkp-fucP, and bearing thus the genes coding for fucose kinase/fucose-1-phosphate guanylyltransferase Fkp and fucose permease FucP. As the genes were cloned in multiple cloning sites (MCS) 1 and 2 of vector pCOLA-Duet-1 (Novagen, UK), expression of both genes can be induced by addition of IPTG, as both MCS are flanked by a T7 promoter/operator on the 5' side.

Both strains were cultured in duplicate in 30 ml 2YT medium, supplemented with kanamycin for the strain with pCOLA-fkp-fucP for plasmid maintenance, at 37° C. and 220 rpm. Induction of Fkp expression was started at $OD_{660}$=0.5 by addition of 1 mM IPTG and both strains were supplied with 20 mM fucose and then cultivated for additional 3 hours at 37° C. and 220 rpm. Cells were pelleted by centrifugation and pellets were resuspended in 5 v/w distilled water. These cell suspensions were incubated at 95° C. for 10 minutes to lyse the cells. Cell debris was removed by centrifugation and the supernatants were analyzed by HPLC.

HPLC analysis was carried out by electrochemical detection with a Decade II pulsed amperometric detector (Antec Leyden, Netherlands). 20 mM sodium hydroxide+825 mM sodium acetate was used as eluent on a CarboPac PA20 column (Dionex, USA). GDP-fucose eluted with a retention time of 16.0 minutes.

TABLE 3

Intracellular GDP-fucose content of *E. coli* JM109 (DE3) ΔfucA with and without expression of fucose kinase/fucose-1-phosphate guanylyltransferase Fkp from pCOLA-fkp-fucP.

| Strain | GDP-fucose content [μM] |
|---|---|
| *E. coli* JM109 (DE3) ΔfucA | not detectable |
| *E. coli* JM109 (DE3) ΔfucA pCOLA-fkp-fucP | 369 μM |

Figure 12A:
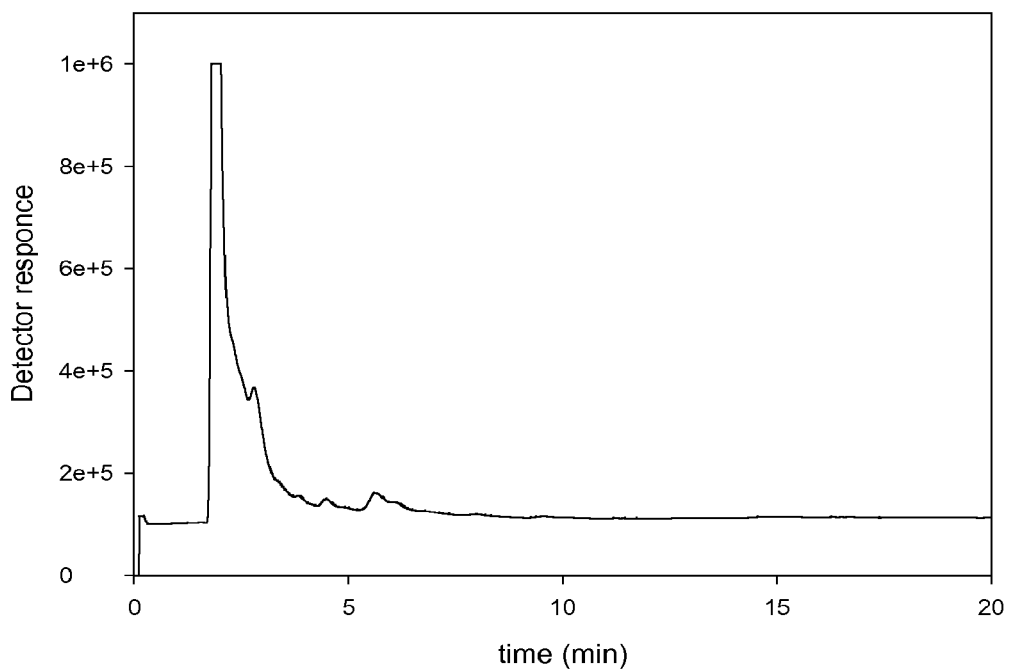
FIG. 12 *a* and *b* show HPLC-analysis with electrochemical detection of GDP-fucose expression in *E. coli* JM109 (DE3) ΔfucA (FIG. 12*a*) and *E. coli* JM109 (DE3) ΔfucA pCOLA-fkp-fucP (FIG. 12*b*).

FIG. 12*a* shows HPLC-analysis of *E. coli* JM109 (DE3) ΔfucA cells for GDP-fucose expression without expression of FKP protein.

Figure 12B:
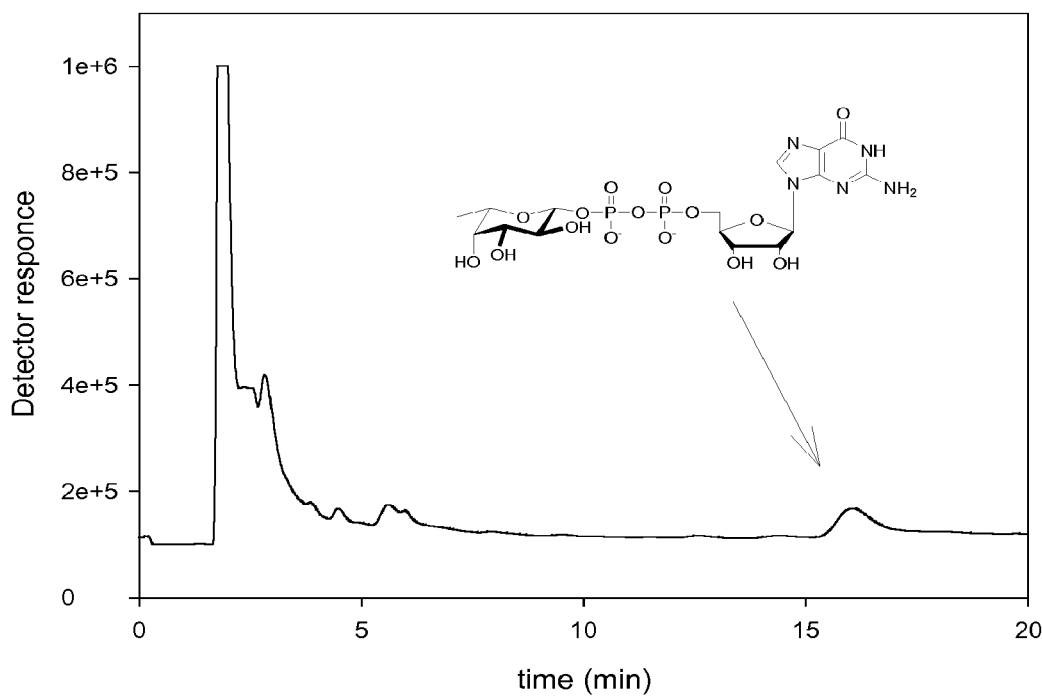

FIG. 12*b* is an analysis of *E. coli* JM109 (DE3) ΔfucA pCOLA-fkp-fucP cells coexpressing the Fkp protein together with the fucose importer FucP. The peak at 16.0 min corresponds to GDP-fucose, as verified with an authentic standard.

REFERENCES

Albermann, C., W. Piepersberg & U. F. Wehmeier, (2001) Synthesis of the milk oligosaccharide 2'-fucosyllactose using recombinant bacterial enzymes. *Carbohydr Res* 334: 97-103.

Andersson, B., O. Porras, L. A. Hanson, T. Lagergard & C. Svanborg-Eden, (1986) Inhibition of attachment of *Streptococcus pneumoniae* and *Haemophilus influenzae* by human milk and receptor oligosaccharides. *J Infect Dis* 153: 232-237.

Appelmelk, B. J., S. L. Martin, M. A. Monteiro, C. A. Clayton, A. A. McColm, P. Zheng, T. Verboom, J. J. Maaskant, D. H. van den Eijnden, C. H. Hokke, M. B. Perry, C. M. Vandenbroucke-Grauls & J. G. Kusters, (1999) Phase variation in *Helicobacter pylori* lipopolysaccharide due to changes in the lengths of poly(C) tracts in alpha3-fucosyltransferase genes. *Infect Immun* 67: 5361-5366.

Appelmelk, B. J., M. C. Martino, E. Veenhof, M. A. Monteiro, J. J. Maaskant, R. Negrini, F. Lindh, M. Perry, G. Del Giudice & C. M. Vandenbroucke-Grauls, (2000) Phase variation in H type I and Lewis a epitopes of *Helicobacter pylori* lipopolysaccharide. *Infect Immun* 68: 5928-5932.

Bergman, M., G. Del Prete, Y. van Kooyk & B. Appelmelk, (2006) *Helicobacter pylori* phase variation, immune modulation and gastric autoimmunity. *Nat Rev Microbiol* 4: 151-159.

Bode, L., (2006) Recent advances on structure, metabolism, and function of human milk oligosaccharides. *J Nutr* 136: 2127-2130.

Coppa, G. V., L. Zampini, T. Galeazzi, B. Facinelli, L. Ferrante, R. Capretti & G. Orazio, (2006) Human milk oligosaccharides inhibit the adhesion to Caco-2 cells of diarrheal pathogens: *Escherichia coli*, *Vibrio cholerae*, and *Salmonella fyris*. *Pediatr Res* 59: 377-382.

Coyne, M. J., B. Reinap, M. M. Lee & L. E. Comstock, (2005) Human symbionts use a host-like pathway for surface fucosylation. *Science* 307: 1778-1781.

Crane, J. K., S. S. Azar, A. Stam & D. S. Newburg, (1994) Oligosaccharides from human milk block binding and activity of the *Escherichia coli* heat-stable enterotoxin (STa) in T84 intestinal cells. *J Nutr* 124: 2358-2364.

Cravioto, A., A. Tello, H. Villafan, J. Ruiz, S. del Vedovo & J. R. Neeser, (1991) Inhibition of localized adhesion of enteropathogenic *Escherichia coli* to HEp-2 cells by immunoglobulin and oligosaccharide fractions of human colostrum and breast milk. *J Infect Dis* 163: 1247-1255.

Datsenko, K. A. & B. L. Wanner, (2000) One-step inactivation of chromosomal genes in *Escherichia coli* K-12 using PCR products. *Proc Natl Acad Sci USA* 97: 6640-6645.

Dower, W. J., J. F. Miller & C. W. Ragsdale, (1988) High efficiency transformation of *E. coli* by high voltage electroporation. *Nucleic Acids Res* 16: 6127-6145.

Dumon, C., C. Bosso, J. P. Utille, A. Heyraud & E. Samain, (2006) Production of Lewis x tetrasaccharides by metabolically engineered *Escherichia coli*. *Chembiochem* 7: 359-365.

Dumon, C., B. Priem, S. L. Martin, A. Heyraud, C. Bosso & E. Samain, (2001) In vivo fucosylation of lacto-N-neotetraose and lacto-N-neohexaose by heterologous expression of *Helicobacter pylori* alpha-1,3 fucosyltransferase in engineered *Escherichia coli*. *Glycoconj J* 18: 465-474.

Dumon, C., E. Samain & B. Priem, (2004) Assessment of the two *Helicobacter pylori* alpha-1,3-fucosyltransferase ortholog genes for the large-scale synthesis of LewisX human milk oligosaccharides by metabolically engineered *Escherichia coli*. *Biotechnol Prog* 20: 412-419.

Ge, Z., N. W. Chan, M. M. Palcic & D. E. Taylor, (1997) Cloning and heterologous expression of an alpha1,3-fucosyltransferase gene from the gastric pathogen *Helicobacter pylori*. *J Biol Chem* 272: 21357-21363.

Gnoth, M. J., S. Rudloff, C. Kunz & R. K. Kinne, (2001) Investigations of the in vitro transport of human milk oligosaccharides by a Caco-2 monolayer using a novel high performance liquid chromatography-mass spectrometry technique. *J Biol Chem* 276: 34363-34370.

Grant, W. D., I. W. Sutherland & J. F. Wilkimson, (1970) Control of colanic acid synthesis. *J Bacteriol* 103: 89-96.

Hinderlich S, Berger, M., Blume, A., Chen, H., Ghaderi, D. & Bauer, C. (2002) Identification of human L-fucose kinase amino acid sequence. *Biochem. Biophys. Res. Commun.* 294, 650-654.

Koizumi, S., T. Endo, K. Tabata, H. Nagano, J. Ohnishi & A. Ozaki, (2000) Large-scale production of GDP-fucose and Lewis X by bacterial coupling. *J Ind Microbiol Biotechnol* 25: 213-217.

Kretzschmar, G. & W. Stahl, (1998) Large scale synthesis of linker-modified sialyl-Lewis(X), Lewis(X) and N-acetyl-lactosamine. *Tetrahedron* 54: 6341-6358.

Kunz, C. & S. Rudloff, (2006) Health promoting aspects of milk oligosaccharides. *Int Dairy J* 16: 1341-1346.

Li, M., X. W. Liu, J. Shao, J. Shen, Q. Jia, W. Yi, J. K. Song, R. Woodward, C. S. Chow & P. G. Wang, (2008) Characterization of a novel alpha1,2-fucosyltransferase of *Escherichia coli* 0128:b12 and functional investigation of its common motif. Biochemistry 47: 378-387.

Ma, B., J. L. Simala-Grant & D. E. Taylor, (2006) Fucosylation in prokaryotes and eukaryotes. *Glycobiology* 16: 158R-184R.

Martin, S. L., M. R. Edbrooke, T. C. Hodgman, D. H. van den Eijnden & M. I. Bird, (1997) Lewis X biosynthesis in *Helicobacter pylori*. Molecular cloning of an alpha(1,3)-fucosyltransferase gene. *J Biol Chem* 272: 21349-21356.

Newburg, D. S., (2001) Bioactive components of human milk: evolution, efficiency, and protection. *Adv Exp Med Biol* 501: 3-10.

Newburg, D. S. & S. H. Neubauer, (1995) Carbohydrates in milk. In: Handbook of Milk Composition. R. G. Jensen (ed). San Diego, Calif.: Academic Press, pp. 273-349.

Rasko, D. A., G. Wang, M. M. Palcic & D. E. Taylor, (2000) Cloning and characterization of the alpha(1,3/4) fucosyltransferase of *Helicobacter pylori*. *J Biol Chem* 275: 4988-4994.

Ruiz-Palacios, G. M., L. E. Cervantes, P. Ramos, B. Chavez-Munguia & D. S. Newburg, (2003) *Campylobacter jejuni* binds intestinal H(O) antigen (Fuc alpha 1, 2Gal beta 1, 4GlcNAc), and fucosyloligosaccharides of human milk inhibit its binding and infection. *J Biol Chem* 278: 14112-14120.

Sambrook, J. & D. W. Russell, (2001) *Molecular cloning: a laboratory manual*. Cold Spring Harbor Laboratory Press, Cold Spring Harbor, N.Y.

Stumpp, T., B. Wilms & J. Altenbuchner, (2000) Ein neues L-Rhamnose-induzierbares Expressionssystem for *Escherichia coli*. BIOspektrum 6: 33-36.

Wang, G., Z. Ge, D. A. Rasko & D. E. Taylor, (2000) Lewis antigens in *Helicobacter pylori*: biosynthesis and phase variation. *Mol Microbiol* 36: 1187-1196.

Wang, G., D. A. Rasko, R. Sherburne & D. E. Taylor, (1999) Molecular genetic basis for the variable expression of Lewis Y antigen in *Helicobacter pylori*: analysis of the alpha (1,2) fucosyltransferase gene. *Mol Microbiol* 31: 1265-1274.

Park, S. H., I. Pastuszak, R. Drake & A. D. Elbein, (1998). Purification to apparent homogenicity and properties of pig kidney L-fucose kinase. *J Biol Chem* 273: 5685-5691.

The invention claimed is:

1. A method for making a fucosyllactose the method comprises cultivating a genetically modified *Escherichia coli* having the ability to produce the fucosyllactose under suitable cultivation conditions in a medium comprising L-fucose and an acceptor substrate, wherein said acceptor substrate is lactose, and wherein the *Escherichia coli* has been transformed to express
   i) a gene encoding a bacterial bifunctional fucose kinase/fucose-1-phosphate guanylyltransferase, wherein the bacterial bifunctional fucose kinase/fucose-1-phosphate guanylyltransferase gene is an fkp gene of *Bacteroides fragilis*, and
   ii) a gene encoding a fucosyltransferase from *Helicobacter*,
wherein at least one gene encoding a protein that functions in the catabolic pathway for fucose, selected from the group consisting of a fucose-1-phosphate aldolase gene (fucA gene), a fucose isomerase gene and a fuculose kinase gene, is inactivated in the *Escherichia coli*.

2. The method of claim 1, wherein the fucosyllactose is 2'-fucosyllactose, 3-fucosyllactose or lactodifucotetraose.

3. The method of claim 1, wherein the fucA gene encoding fucose-1-phosphate aldolase is deleted.

4. The method of claim 1, wherein the fucosyllactose is 2'-fucosyllactose and the fucosyltransferase is an alpha-1,2-fucosyltransferase encoded by the *Helicobacter pylori* NCTC364 fucT2 gene.

5. The method of claim 1, the fucosyllactose is 3-fucosyllactose and the fucosyltransferase is an alpha-1,3-fucosyltransferase encoded by the *Helicobacter pylori* 26695 futA gene.

* * * * *